(12) United States Patent
Seis et al.

(10) Patent No.: US 11,679,174 B2
(45) Date of Patent: Jun. 20, 2023

(54) CLEANING INDICATOR (71) Applicant: Mesa Laboratories, Inc., Lakewood, CO (US)

(72) Inventors: Toni Seis, München-Riem (DE); Charlie McLaughlin, Bozeman, MT (US); Pete Jung, Lakewood, CO (US); Sven Kasemann, München-Riem (DE)

(73) Assignee: Mesa Laboratories, Inc., Lakewood, CO (US)

( * ) Notice: Subject to any disclaimer, the term of this patent is extended or adjusted under 35 U.S.C. 154(b) by 175 days.

(21) Appl. No.: 17/229,378

(22) Filed: Apr. 13, 2021

(65) Prior Publication Data
US 2022/0001064 A1 Jan. 6, 2022

Related U.S. Application Data (60) Provisional application No. 63/046,940, filed on Jul. 1, 2020.

(51) Int. Cl.
A61L 2/28 (2006.01)
G01M 99/00 (2011.01)

(52) U.S. Cl.
CPC ............. *A61L 2/28* (2013.01); *G01M 99/005* (2013.01); *A61L 2202/24* (2013.01)

(58) Field of Classification Search
CPC .......................... G01M 99/005; A61L 2202/24
See application file for complete search history.

(56) References Cited

U.S. PATENT DOCUMENTS

| 4,636,472 A | 1/1987 | Bruso | |
| 2006/0218994 A1* | 10/2006 | Lin | B09B 3/00 73/60.11 |
| 2007/0074742 A1 | 4/2007 | Lin et al. | |

(Continued)

FOREIGN PATENT DOCUMENTS

| CN | 207722140 U | 8/2018 | |
| DE | 2744938 A * | 6/1978 | ........... A63H 33/065 |

(Continued)

OTHER PUBLICATIONS

Machine translation of JP2837378B2 (Year: 1998).*

(Continued)

*Primary Examiner* — Patrick Assouad
*Assistant Examiner* — Sangkyung Lee
(74) *Attorney, Agent, or Firm* — Breiner & Breiner, L.L.C.

(57) ABSTRACT

A cleaning indicator is disclosed for determining the effectiveness of a washing and disinfecting process related to the healthcare, medical device and pharmaceutical fields. The cleaning indicator includes a base, a soil coupon and a cover. The base has a recessed area for receiving the soil coupon and the cover is attached to the base by clip members. The cover has a transparent window for viewing the soil coupon which transparent window optionally may have a small hole therein. The base includes grip members for attaching the cleaning indicator to a tray in a washer-disinfector. The cleaning indicator is placed in the washer-disinfector for medical instruments or the like for determining the efficacy of the wash cycle of the washer-disinfector.

17 Claims, 5 Drawing Sheets (56) References Cited

U.S. PATENT DOCUMENTS

| | | | | |
|---|---|---|---|---|
| 2013/0089922 | A1* | 4/2013 | Franciskovich | A61L 2/28 422/417 |
| 2016/0327490 | A1* | 11/2016 | Frieze | A61B 90/70 |
| 2019/0307911 | A1 | 10/2019 | Bala | |

FOREIGN PATENT DOCUMENTS

| | | | | |
|---|---|---|---|---|
| DE | 29909783 | U1 | 12/1999 | |
| DE | 102004040733 | A1 | 3/2006 | |
| DE | 102005000926 | A1 | 7/2006 | |
| JP | 2837378 | B2 * | 12/1998 | |
| JP | 4720646 | B2 * | 7/2011 | B60N 3/023 |
| WO | 2008121792 | A2 | 10/2008 | |
| WO | 2016084398 | A1 | 6/2016 | |

OTHER PUBLICATIONS

Machine translation of DE2744938A (Year: 1978).*
Machine translation of JP 4720646BB2 (Year: 2011).*
TOSI® Test System, Healthmark Industries, https://www.hmark.com/tosi.php, two pages, Jul. 2, 2021.
Serim® Research Corporation, Pinnacle Monitor For Automated Enzymatic Cleaning 9AEC) Process, Overview, 13 Pages, May 2020.
VERIFY® All Clean Test Washer Indicator, https://steris.com; Mentor, Ohio, 3 Pages.
SteriTec Products Mfg., Co., Inc., Englewood, Colorado, Wash-Checks Cleaning Monitor WC 101, WC 101/50, vww.getinge.com/steritec, 1 Page.
Simicon GmbH, Munchen, Germany, SIMICON RI Product Brochure, Sep. 2017, 4 Pages.

* cited by examiner

CLEANING INDICATOR

RELATED APPLICATION

This application claims benefit of U.S. Provisional Application Ser. No. 63/046,940, filed Jul. 1, 2020, entitled "Cleaning Indicator," which application is incorporated herein by reference in its entirety.

FIELD OF THE INVENTION

The present invention relates to cleaning indicators to determine the effectiveness of a washing and disinfecting process. More particularly, the invention relates to a cleaning indicator for determining the effectiveness of a washing and disinfecting process related to the healthcare and pharmaceutical fields.

BACKGROUND OF THE INVENTION

Washer-disinfectors are used in the healthcare industry for cleaning medical instruments and the like, e.g. the Miele PG 8536 washer-disinfector. Standards for washer-disinfectors may be found in ISO 15883-1:2006, which is incorporated herein by reference. Such instruments may include blood or other materials on them requiring a thorough cleaning and subsequent disinfection. For validation and routine monitoring of cleaning processes using a washer-disinfector, cleaning indicators are used to determine the efficacy of the cleaning process and identify any potential sources of error in the cleaning process. Thus, cleaning is the critical first step performed prior to disinfection and sterilization. If debris is left on an instrument, this may interfere with the microbial inactivation and can compromise the disinfection or sterilization processes. Cleaning indicators compliment the sterilization process within the central sterile supply department in hospitals.

Cleaning indicators are known on the market, including the Tosi® test system sold by Healthmark Industries, Inc. to enable one to verify the cleaning efficacy of a washer-disinfector during routine operation and said to be covered by German Utility Model DE29909783 which is incorporated herein by reference. The cleaning indicator is processed together with the materials to be cleaned such as surgical instruments. The cleaning indicator is provided with a test soil in order to check the removal of, among other things, human blood and polysaccharides. In the case of an optimal test result, a perfect cleaning of the instruments is said to be guaranteed. In the case of an inadequate test result, measures must be taken to provide for an effective wash cycle. Other cleaning indicators on the market include the Simicon RI system; the Serim® Pinnacle Monitor For Automated Enzymatic Cleaning Process; the Steris Verify All Clean Test Washer Indicator; and the SteriTec WC 101 Wash-Checks for use with the WC 102 Wash-Checks Holder.

While the known cleaning indicators have provided a device for determining the efficacy of the washer-disinfector process, some cleaning indicators are held loose in the washer-disinfector and may move during the process or may not be adequately treated with the spray from the washer-disinfector. Other of these products are expensive to manufacture due to the materials in which they are made, e.g. stainless steel. Further, other drawbacks of the known cleaning indicators include an indicator which provides an unclear result, or a result that is deciphered differently from user to user. Additionally, the soil coupon holder and soil coupon for some cleaning indicators are sold separately. These cleaning indicators will require additional user training for inserting the soil coupon in the holder, leading to possible inconsistent results of the wash cycles cleaning with different users.

Accordingly, the known cleaning indicators have various shortcomings. These and other shortcomings of the known devices are addressed by the present invention.

SUMMARY OF THE INVENTION

It is a primary object of the invention to provide a cleaning indicator for use in a washer-disinfector to assess the efficacy of a cleaning process of the washer-disinfector.

It is another primary object of the invention to provide a cleaning indicator having a base, a soil coupon and a cover wherein the base has one or more grip members for attachment to the washer-disinfector.

It is another primary object of the invention to provide a cleaning indicator having a base, a soil coupon and a cover wherein the base includes a recessed area in the top portion of the base for receiving and holding the soil coupon.

It is another primary object of the invention to provide a cleaning indicator having a base, a soil coupon and a cover wherein the cover has clips for attachment of the cover to the base.

It is another primary object of the invention to provide a cleaning indicator having a base, a soil coupon and a cover wherein the cover includes a transparent window for viewing of the soil coupon.

It is another primary object of the invention to provide a cleaning indicator having a base, a soil coupon and a cover wherein the cover and the base are transparent.

It is another primary object of the invention to provide a cleaning indicator having a base, a soil coupon and a cover wherein the cover has a transparent window having an opening therein.

It is another primary object of the invention to provide a cleaning indicator having a base, a soil coupon and a cover wherein the cover has tabs extending downwardly from a bottom portion of the cover to hold in place the soil coupon.

It is another primary object of the invention to provide a single use cleaning indicator which will reduce placement errors of the soil coupon in the indicator, thereby increasing consistency between wash cycles and the end-users.

It is another primary object of the invention to provide a cleaning indicator which is easy and inexpensive to manufacture and simple to use in a washer-disinfector.

It is another primary object of the invention to provide a cleaning indicator wherein the soil coupon may be removed from the cleaning indicator after cleaning to perform additional testing on the soil coupon such as protein verification tests.

The present invention is directed to a cleaning indicator comprising a base, a cover and a soil coupon. The base includes a top portion and a bottom portion. The top portion of the base includes a recessed area for receiving the soil coupon and a bracket at each end thereof for retaining the soil coupon. The bottom portion of the base includes one or more grip members for attaching the cleaning indicator to a tray in a washer-disinfector. In one embodiment, the base is transparent. The soil coupon includes a substrate which is preferably made of stainless steel and constructed to fit into the recessed area of the base. A soil sample is placed or coated on the substrate. The soil coupon is placed in the recessed area of the base. The cover is attached to the base. The cover includes a top portion and a bottom portion. The cover includes a transparent window for viewing the soil coupon in the base or the entire cover may be transparent. There is optionally a small opening in the transparent window and over the soil coupon. The cover includes at least two clips for attaching the cover to the base, and there are at least two tabs extending downwardly from the bottom portion of the cover to hold the soil coupon in the base when the cover is attached to the base. In a preferred embodiment, the cleaning indicator is a single use cleaning indicator sold as an entire unit such that the user does not need to insert the soil coupon. The assembled cleaning indicator is placed in the washer-disinfector and the grip members attach to a mesh tray of the washer-disinfector. A cleaning indicator is preferably attached to each tray of the washer-disinfector. Cleaning fluid from the washer-disinfector will treat the soil coupon through the openings at the sides of the cleaning indicator. If the cover includes a small opening, the cleaning indicator fluid will also treat the soil coupon through the hole in the top of the cover. At the completion of the wash cycle, the cleaning indicator will allow viewing through the window in the cover to see if the soil has been completely removed, indicating an optimal wash cycle. The cover may be removed from the base to further examine the soil coupon. If some or all of the soil sample remains on the soil coupon, the wash cycle has failed and the instruments should not be sent to sterilization and the washer-disinfector must undergo trouble shooting pursuant to the end-user's standard operating procedures or the manufacturer's recommendations for a failed wash cycle.

These primary and other objects of the invention will be apparent from the following description of the preferred embodiments of the invention and from the accompanying drawings.

BRIEF DESCRIPTION OF THE DRAWINGS

The following detailed description of the specific non-limiting embodiments of the present invention can be best understood when read in conjunction with the following drawings, where like structures are indicated by like reference numbers.

Referring to the drawings.

DETAILED DESCRIPTION OF THE PREFERRED EMBODIMENTS

Figure 8:
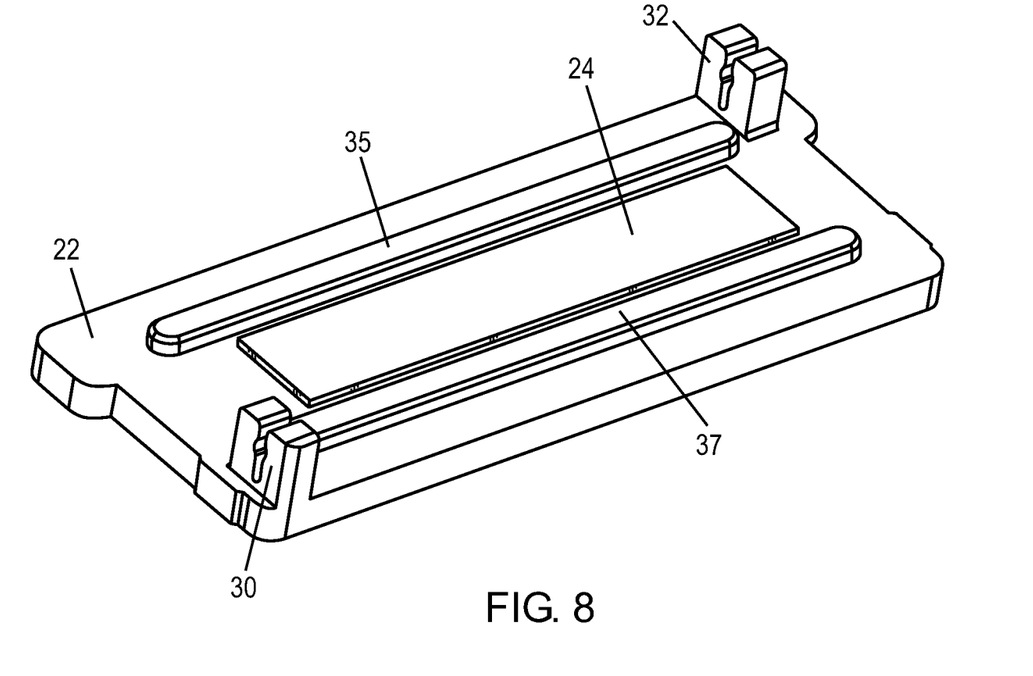
FIG. 8 is a perspective view of an alternative embodiment of the bottom portion of a base of the cleaning indicator of FIG. 1.
Figure 9:
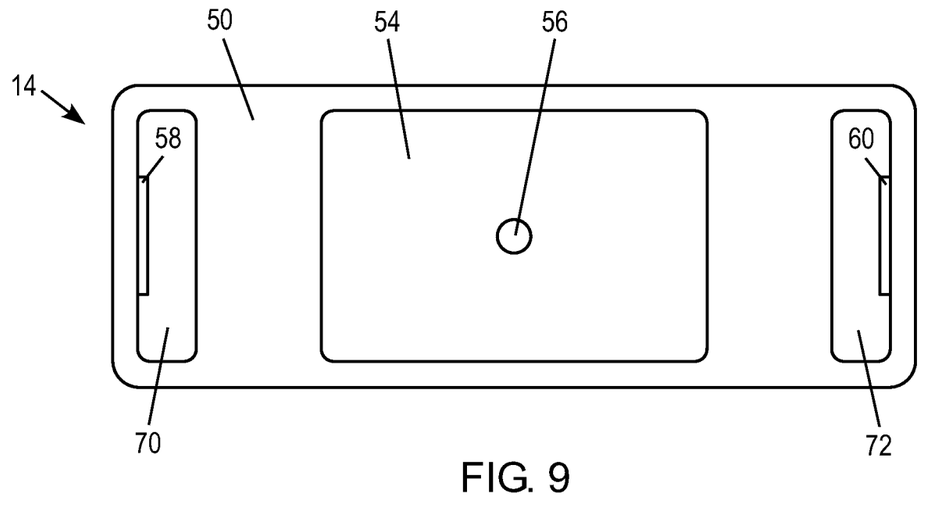
FIG. 9 is a top view of an alternative embodiment of the cover of a cleaning indicator of FIG. 1.
Figure 10:
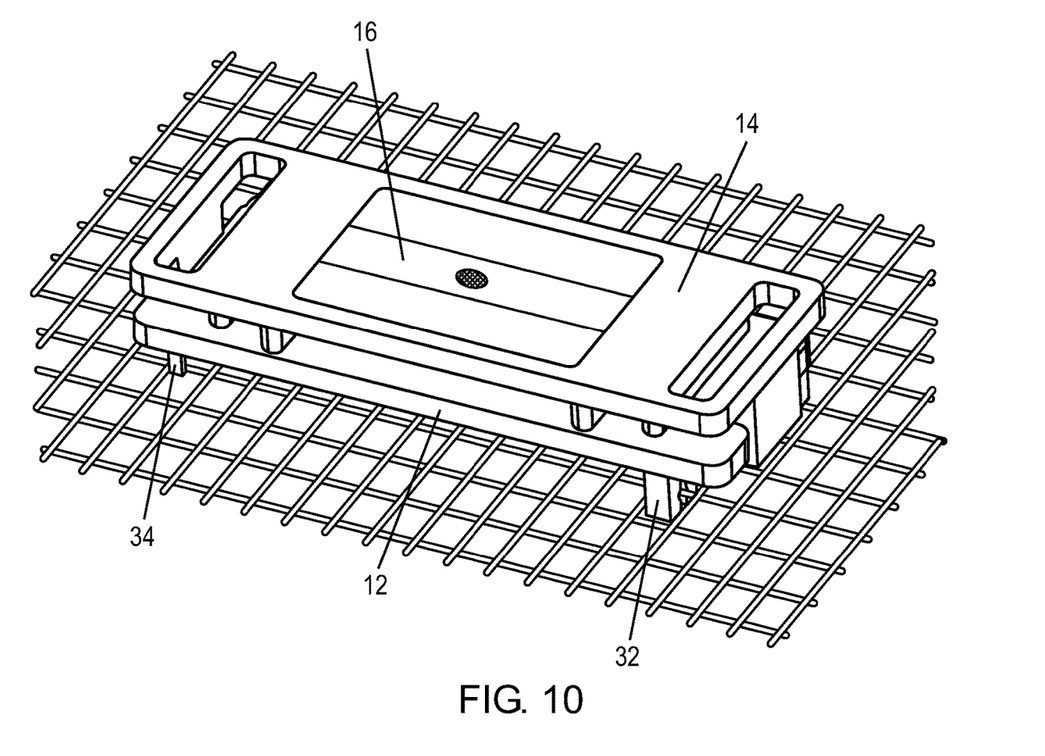
FIG. 10 is a perspective view of the cleaning indicator of FIG. 1 in a tray of a washer-disinfector.

The present invention is directed to a cleaning indicator for determining the effectiveness of a washing and disinfecting process of a washer-disinfector and related to the healthcare and pharmaceutical fields. The cleaning indicator includes a base, a cover and a soil indicator. The base and cover are preferably made of a durable and resilient plastic material such as polycarbonate, although other plastics may be used without departing from the scope of the invention, e.g. high density polyethylene. The base and cover are preferably made by injection molding. The cleaning indicator is preferably about 48 mm by 18 mm with a height of about 10.5 mm. In a preferred embodiment, the cleaning indicator is a single use cleaning indicator. FIGS. 1-7 illustrate the cleaning indicator of the invention. FIG. 8 shows an alternative embodiment of the base of the cleaning indicator. FIG. 9 shows an alternative embodiment of the cover of the cleaning indicator. FIG. 10 shows the cleaning indicator of FIGS. 1-7 attached to a tray of a washer-disinfector.

Figure 1:
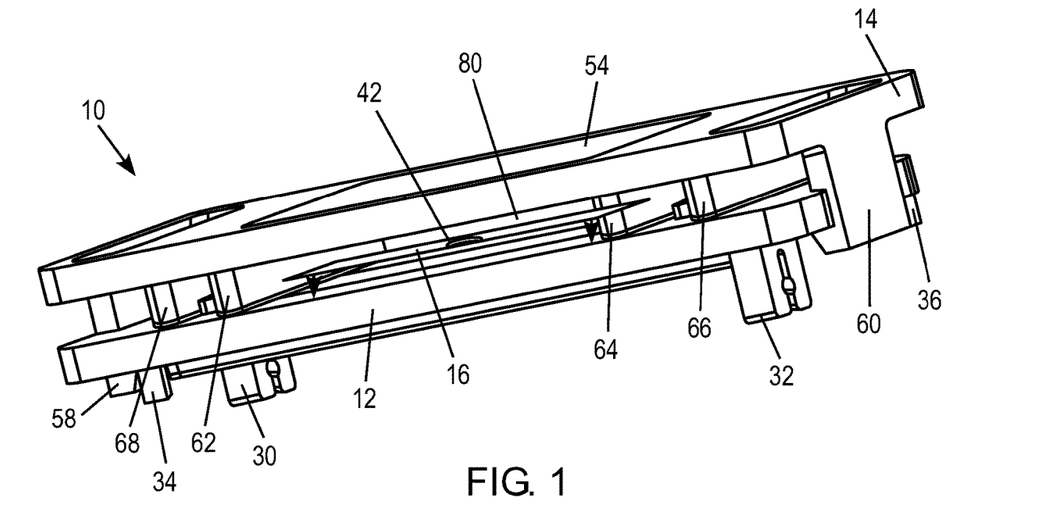
FIG. 1 is a perspective view of the cleaning indicator of the present invention.
Figure 2:
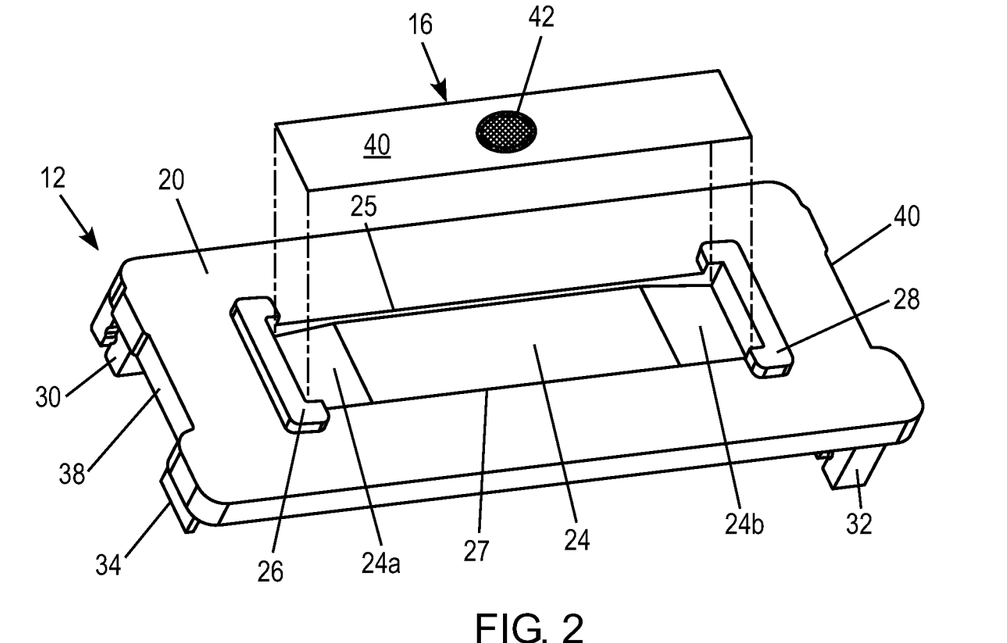
FIG. 2 is a perspective view of the top portion of the base of the cleaning indicator of FIG. 1.

Referring to FIGS. 1-7, there is shown a cleaning indicator 10. The cleaning indicator 10 comprises a base 12, a cover 14 and a soil coupon 16. The soil coupon 16 is shown in FIGS. 1 and 2 not in recess 24 of base 12 for ease of reference.

Figure 3:
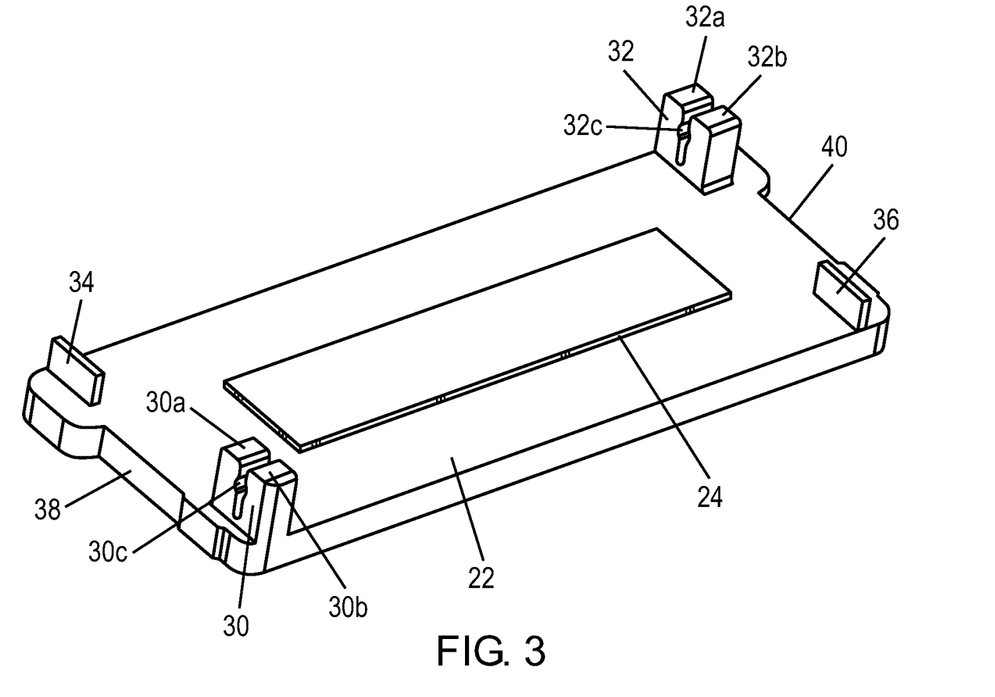
FIG. 3 is a perspective view of the bottom portion of the base of the cleaning indicator of FIG. 1.

Referring to FIGS. 2 and 3, the base 12 includes a top portion 20 and a bottom portion 22. The top portion 20 of the base includes a recessed area 24 for receiving the soil coupon 16 and a bracket 26, 28 at each end thereof for retaining the soil coupon 16. Recessed area 24 may include one or more deeper recessed areas 24a and 24b which allows for easier removal of the soil coupon from the recessed area. The bottom portion 22 of the base includes one or more grip members 30, 32 for attaching the cleaning indicator to a tray of a washer-disinfector. Grips 30 and 32 include legs 30a, 30b and 32a, 32b with groove 30c and 32c for attaching cleaning indicator 10 to a washer-disinfector tray as shown in FIG. 10. The bottom portion 22 may include legs 34, 36 to provide structural support when the cleaning indicator 10 is attached to the tray of a washer-disinfector. The base 12 includes slots 38 and 40 for receiving the clips 58 and 60. Referring to FIG. 8, there is shown an alternative embodiment of base 12 wherein the bottom portion 22 may further include ribs 35, 37 to provide structural support to base 12 and cleaning indicator 10.

Referring to FIG. 3, the soil coupon 16 includes a substrate 40 which is preferably made of stainless steel and constructed to fit into the recessed area 24 of the base 12. A soil sample 42 is placed or coated on the substrate. The soil sample may be in accord with ISO 15883 or as otherwise known in the art.

Figure 4:
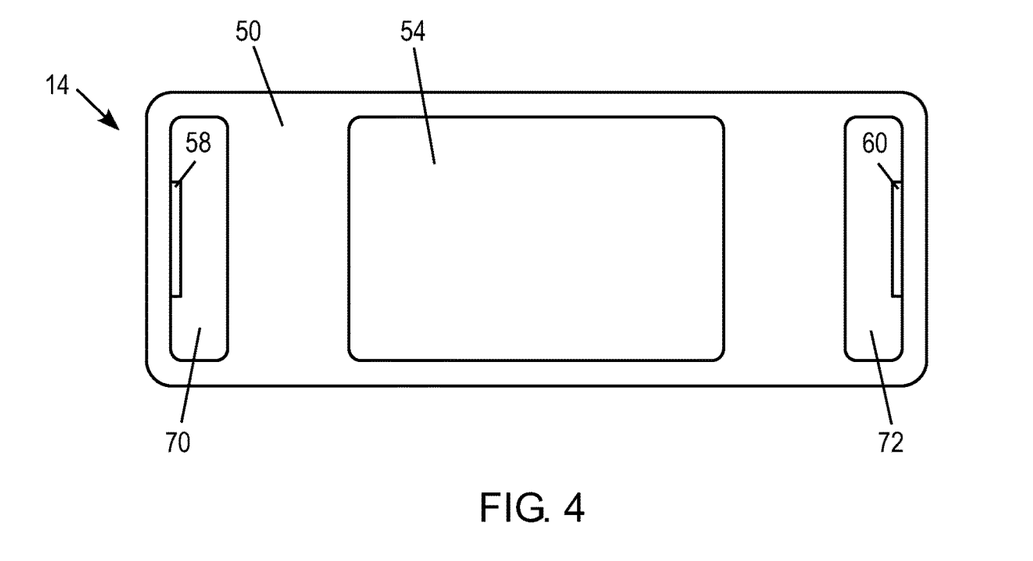
FIG. 4 is a top view of the cover of cleaning indicator of FIG. 1.
Figure 5:
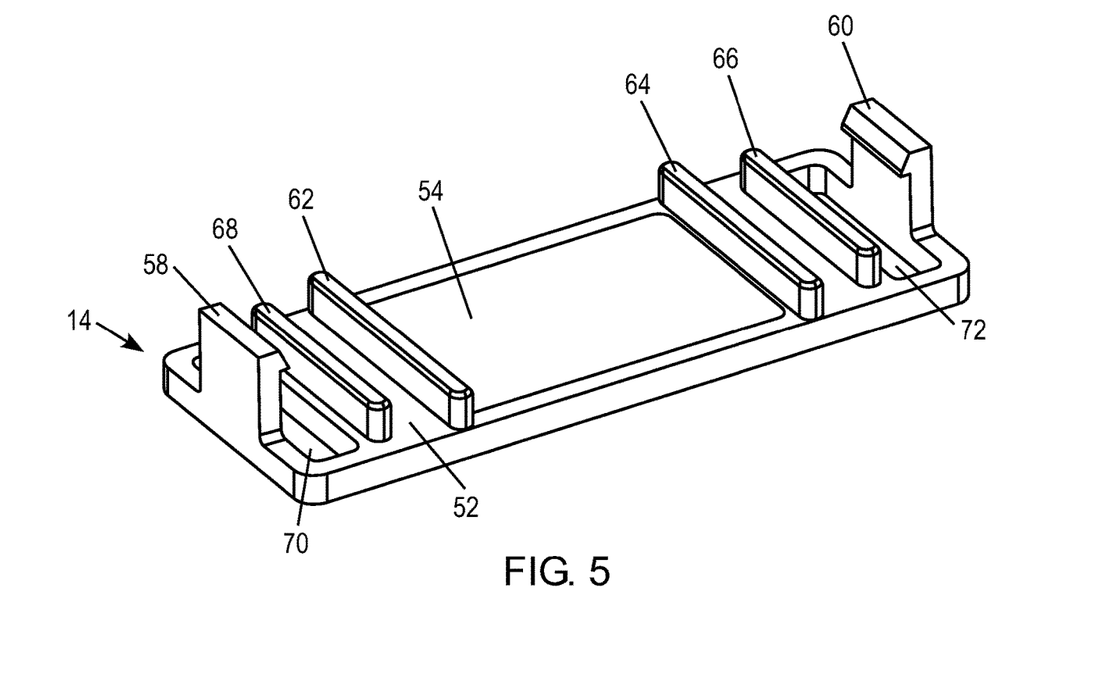
FIG. 5 is a perspective view of the bottom portion of the cover of the cleaning indicator of FIG. 1.
Figure 6:
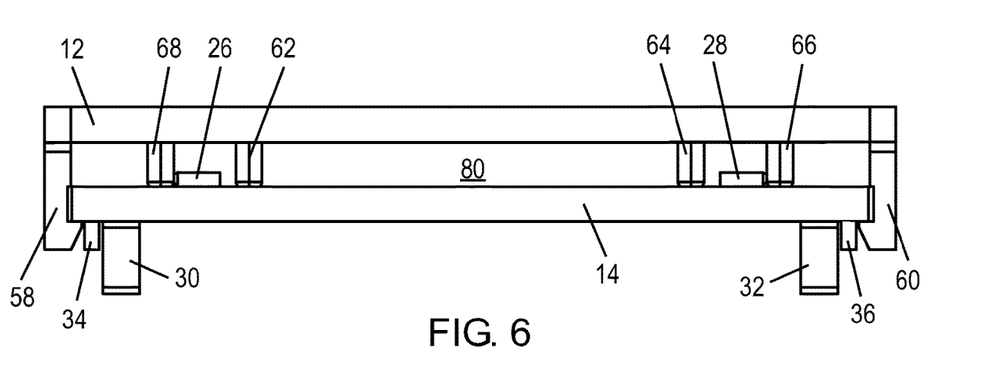
FIG. 6 is a side view of the cleaning indicator of FIG. 1.
Figure 7:
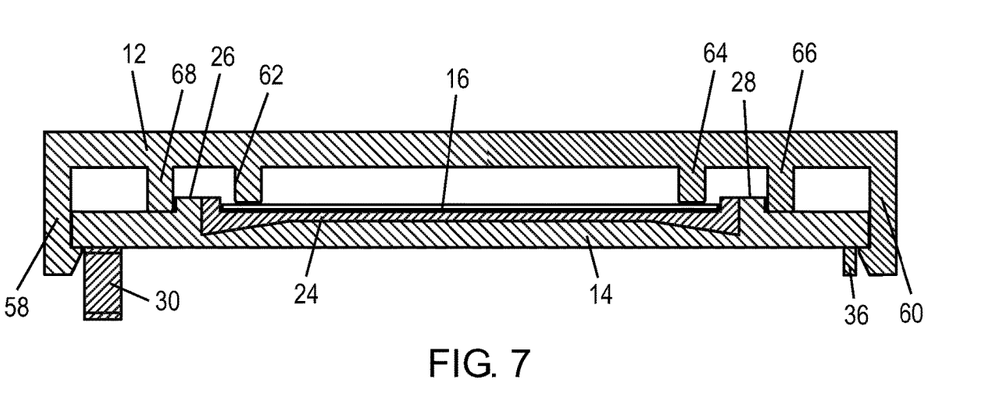
FIG. 7 is a cross-section of the cleaning indicator of FIG. 6.

Referring to FIGS. 4 and 5, the cover 14 includes a top portion 50 and a bottom portion 52. The cover includes at least a transparent window 54 for viewing the soil coupon 16 in the base 12. The window is preferably about 15 mm by 20 mm. The cover includes at least two clips 58 and 60 for attaching the cover to the base 12 at slots 38 and 40. In the alternative, other attachment means may be used such as a slide mechanism. There are at least two tabs 62, 64 extending downwardly from the bottom portion 52 of the cover to hold the soil coupon 16 in the base when the cover is attached to the base. There may also be tabs 66 and 68 which provide additional structural support to the cleaning indicator and align and engage with brackets 26 and 28. The cover may further include openings 70 and 72 providing resiliency to the clips 58 and 60 when attaching the cover 14 to base 12 and a means for gripping the cover 14 when removing the cover from the base. Referring to FIG. 9, there is shown an alternative embodiment of cover 14 wherein the transparent window 54 further includes a small opening 56 over the soil coupon. The opening 56 is preferably about 2 mm.

The soil coupon 16 is inserted into the recessed area 24 of the base and held there by the side walls 25, 27 and brackets 26 and 28 of the recessed area. The cover is attached to the base by clips 58 and 60 at slots 38 and 40. The assembled cleaning indicator 10 includes opening 80 to allow the cleaning material to reach the soil indicator 16. The cleaning indicator is placed in the washer-disinfector and the grip members 30 and 32 attach to a mesh tray of the washer-disinfector as shown in FIG. 10. A cleaning indicator 10 is preferably attached to each tray of the washer-disinfector. Water and cleaning material from the washer-disinfector will treat the soil coupon through the opening 80 at the sides of the cleaning indicator. Where the cover of FIG. 9 is used, water and cleaning material from the washer-disinfector will also treat the soil coupon through the hole 56 in the top of the cover. At the completion of the wash cycle, the cleaning indicator will be viewable through the window 54 in the cover 14 to see if the soil 42 has been completely removed, indicating an optimal wash cycle. The cover may be removed from the base to further examine the soil coupon. If some or all of the soil sample remains on the soil coupon, the wash cycle has failed and the instruments should not be sent to sterilization and the washer-disinfector must undergo trouble-shooting pursuant to the end-user's standard operating procedures or the manufacturer's recommendations for a failed wash cycle.

The embodiments shown are preferably made of polycarbonate and have the transparent window 54. However, the base and cover may be fully transparent.

The exemplary embodiments herein disclosed are not intended to be exhaustive or to unnecessarily limit the scope of the invention. The exemplary embodiments were chosen and described in order to explain the principles of the present invention so that others skilled in the art may practice the invention. As will be apparent to one skilled in the art, various modifications can be made within the scope of the aforesaid description. Such modifications being within the ability of one skilled in the art form a part of the present invention and are embraced by the appended claims.

It is claimed:

1. A cleaning indicator for a washer-disinfector comprising a base, a cover and a soil coupon,
    the base having a top portion and a bottom portion, the top portion of the base having a recessed area adapted to receive the soil coupon and a bracket at each end thereof for retaining the soil coupon, the bottom portion of the base having at least one grip member adapted to attach the cleaning indicator to a tray of the washer-disinfector;
    the soil coupon having a substrate adapted to fit into the recessed area of the base and a soil sample on the substrate;
    the cover having a top portion and a bottom portion, the cover includes a transparent window adapted to view the soil sample in the base, at least two clips adapted to attach the cover to the base and at least two tabs extending downwardly from the bottom portion of the cover adapted to hold the soil coupon in the base when the cover is attached to the base; and
    wherein the soil coupon is inserted into the recessed area of the base and the cover is attached to the base.

2. The cleaning indicator according to claim 1 wherein the recessed area of the base includes at least one deeper recessed area.

3. The cleaning indicator according to claim 1 wherein the bottom portion of the base includes two grip members, one at each end of the base.

4. The cleaning indicator according to claim 3 wherein the bottom portion of the base further includes at least one downwardly extending leg adapted to seat on the tray of the washer-disinfector.

5. The cleaning indicator according to claim 4 wherein each grip member comprises two legs and each leg having a groove area.

6. The cleaning indicator according to claim 1 wherein the cover includes an opening at each end of the cover.

7. The cleaning indicator according to claim 5 wherein the cover includes an opening at each end of the cover.

8. The cleaning indicator according to claim 1 wherein the cover includes an opening in the transparent window.

9. The cleaning indicator according to claim 1 wherein the bottom portion of the base includes at least one rib.

10. The cleaning indicator according to claim 1 wherein the cover and the base of the cleaning indicator are constructed and arranged to provide an opening at each side of the cleaning indicator and adapted to receive a cleaning fluid of the washer-disinfector.

11. The cleaning indicator according to claim 1 wherein the cleaning indicator is substantially rectangular in shape.

12. A method of determining the effectiveness of a washer-disinfector using a cleaning indicator according to claim 1 comprising the steps of
    a. attaching the cleaning indicator to a tray of the washer-disinfector by the at least one grip member,
    b. running a full cycle of the washer-disinfector,
    c. removing the cleaning indicator from the washer-disinfector, and
    d. inspecting the cleaning indicator through the transparent window to determine whether the soil sample has been removed from the soil coupon.

13. A cleaning indicator for a washer-disinfector comprising a base, a cover and a soil coupon,
    the base having a top portion and a bottom portion and being substantially rectangular in shape, the top portion of the base having a recessed area adapted to receive the soil coupon and a bracket at each end thereof for retaining the soil coupon, the bottom portion of the base having at least one grip member at each end of the base and adapted to attach the cleaning indicator to a tray of the washer-disinfector;
    the soil coupon comprising a substantially rectangular substrate adapted to fit into the recessed area of the base and a soil sample on the substrate;
    the cover having a top portion and a bottom portion and being substantially rectangular in shape, the cover includes a transparent window adapted to view the soil sample in the base, at least two clips adapted to attach the cover to the base and at least two tabs extending downwardly from the bottom portion of the cover adapted to hold the soil coupon in the base when the cover is attached to the base;
    wherein the soil coupon is inserted into the recessed area of the base and the cover is attached to the base; and
    wherein the cover and the base of the cleaning indicator are constructed and arranged to provide an opening at each side of the cleaning indicator and adapted to receive a cleaning fluid of the washer-disinfector.

14. The cleaning indicator according to claim 13 wherein the recessed area of the base includes at least one deeper recessed area.

15. The cleaning indicator according to claim 14 wherein the bottom portion of the base further includes at least one downwardly extending leg adapted to seat on the tray of the washer-disinfector.

16. The cleaning indicator according to claim 15 wherein each grip member comprises two legs and each leg having a groove area.

17. The cleaning indicator according to claim 13 wherein the cover includes an opening in the transparent window.

* * * * *